United States Patent [19]

Provost

[11] Patent Number: 5,821,128
[45] Date of Patent: Oct. 13, 1998

[54] METHOD FOR DIFFERENTIATING AND ISOLATING SUB-POPULATIONS OF LEUCOCYTES IN BLOOD SAMPLES BY TREATMENT WITH POLYXOXYETHYLENE 9-LAURYL ETHER, AND REAGENT FOR ITS IMPLEMENTATION

[75] Inventor: René Provost, Chateaugiron, France

[73] Assignee: Hycel Diagnostics, Pouilly En Auxois, France

[21] Appl. No.: 663,348

[22] Filed: Jun. 13, 1996

[30] Foreign Application Priority Data

Jun. 13, 1995 [FR] France .................................. 95 07006

[51] Int. Cl.⁶ ........................... G01N 33/48; G01N 31/00
[52] U.S. Cl. .................................. 436/63; 436/8; 436/10; 436/17; 436/174; 436/175; 435/2; 435/29; 435/30; 435/34; 252/408.1
[58] Field of Search ..................... 436/8, 10, 17, 436/63, 174, 175; 435/2, 29, 30, 34, 39; 252/408.1

[56] References Cited

U.S. PATENT DOCUMENTS

| | | | |
|---|---|---|---|
| 4,153,689 | 5/1979 | Hirai et al. ................................... | 514/3 |
| 4,610,961 | 9/1986 | Guardino et al. .......................... | 435/34 |
| 5,196,346 | 3/1993 | Lefevre et al. ............................ | 436/63 |
| 5,227,304 | 7/1993 | Wong ......................................... | 436/17 |
| 5,250,438 | 10/1993 | Ryan .......................................... | 436/17 |
| 5,389,549 | 2/1995 | Hamaguchi et al. ...................... | 436/10 |
| 5,413,732 | 5/1995 | Buhl et al. .......................... | 252/182.11 |
| 5,413,938 | 5/1995 | Tsujino et al. ............................ | 436/63 |
| 5,496,734 | 3/1996 | Sakata ....................................... | 436/63 |
| 5,518,928 | 5/1996 | Cremins et al. .......................... | 436/40 |
| 5,538,893 | 7/1996 | Sakata et al. ............................. | 436/10 |
| 5,618,733 | 4/1997 | Sakata et al. ............................. | 436/17 |

FOREIGN PATENT DOCUMENTS

| | | |
|---|---|---|
| 0325710 | 8/1989 | European Pat. Off. . |
| 0424871A1 | 5/1991 | European Pat. Off. . |
| 0442776A1 | 8/1991 | European Pat. Off. . |
| 0444240A1 | 9/1991 | European Pat. Off. . |
| 0617281A3 | 9/1994 | European Pat. Off. . |
| 0678743A1 | 10/1995 | European Pat. Off. . |

OTHER PUBLICATIONS

Sigma Chemical Company Catalog, 1993, p. 824.

*Primary Examiner*—Maureen M. Wallenhorst
*Attorney, Agent, or Firm*—Jacobson, Price, Holman & Stern, PLLC

[57] ABSTRACT

A method for differentiating and isolating sub-populations of leucocytes in a blood sample involved treating the sample with polyoxyethylene 9-lauryl ether. This method is suitable for isolating basophil granulocytes when it is conducted in an acid medium.

15 Claims, No Drawings

METHOD FOR DIFFERENTIATING AND ISOLATING SUB-POPULATIONS OF LEUCOCYTES IN BLOOD SAMPLES BY TREATMENT WITH POLYXOXYETHYLENE 9-LAURYL ETHER, AND REAGENT FOR ITS IMPLEMENTATION

FIELD OF THE INVENTION

This invention relates to a method for differentiating and isolating sub-populations of leucocytes in blood samples by treatment with polyoxyethylene 9-lauryl ether.

It also relates to a reagent for implementing this method.

BACKGROUND

The object of haematological analysis is to identify and count several categories of cells in order to establish a diagnosis. The cells to be identified are usually leucocytes divided into three families, namely lymphocytes, monocytes and granulocytes. The latter comprise, in particular, eosinophils, neutrophils and basophils.

Such analysis is generally carried out with means which use the Coulter effect. Such means involves the passage of the cells in a conducting liquid through an opening of small diameter to which is applied a constant electric current. The passage of a particle at this point produces a transient variation of conductivity corresponding to the volume occupied by the particle as it passes through the opening.

These measurements of variation in impedance are, however, known to be insufficient for cell identification. Cells belonging to different families sometimes have very similar volumes.

This is the reason why, in addition to these measurements of impedance variation, other measurements are conventionally made using an optical device such as a laser diode. With this type of device, the cells passing through an opening of small diameter are illuminated by a laser beam and reflect the light. The intensity of the light reflected by a cell is in correlation with the refractive index of this cell. Measurement of the reflected light therefore gives information on the surface condition of the cell.

It is found that by using information on cell volume and surface condition, it is possible to obtain a precise analysis.

Whichever means are used for haematological analysis, blood samples for analysis must be prepared previously.

The count of sub-populations of basophil granulocytes is particularly difficult to perform as in most samples of human blood they are present in very low proportions, generally less than 1% of the total number of leucocytes.

Also, cases of hyperbasophilia are very rare, that is to say cases in which there are a high number of basophil granulocytes, which makes the study of these cells all the more difficult.

Solutions have been put forward to solve the problem of isolating, differentiating and counting these cells.

Thus, patent application EP-325 710 (TOA MEDICAL ELECTRONICS) relates to a composition for the quantification of leucocytes and haemoglobin, comprising at least one non-ionic surface active agent comprising from 6 to 50 polyoxyethylene groups. Only surface active agents having a $C_{16}$ or $C_{18}$ fatty acid residue are disclosed.

European patent application EP-177 137 disclosed a reagent which produces progressive deterioration of all blood cells with the exception of basophil polynuclear cells. The reagent used to treat blood samples comprises a surface active agent which may be an ether of a $C_6$ to $C_{16}$ aliphatic alcohol and of a glycol polyalkylene, mixed with a sulphonic, carboxylic or hydrochloric acid.

The only compound whose structure has been precisely identified, and which was tested in this patent application, is polyoxyethylene 23-lauryl ether, marketed under the name Brij 35.

This reagent nevertheless has two main disadvantages. Firstly, the time required to obtain full lysis of the cells other than the basophil granulocytes, is more than 80 seconds, which is too long for use on automated cytology counters.

Also, this reagent does not achieve full lysis of the blood cells other than the granulocytes. Numerous cell debris resulting from this incomplete lysis are therefore present in the lysed samples, which leads to blocking the count openings of automated cytometers.

A complex reagent containing polyoxyethylene 23-lauryl ether, in a mixture with SDS, phthalic acid and hydrochloric acid in particular, was proposed in patent application FR 2 658 300, published Aug. 16, 1991, under National Registration No. 90 01660, in order to solve this problem. However, the quality of the preparations obtained after treatment of blood samples with this reagent is not always satisfactory owing to the presence of too many debris, and it is impossible to obtain reproducible results. Cloudiness was observed after mixing the blood sample with the lysis reagent making any measurement impossible.

Also, this method can only differentiate the basophil granulocytes and not the eosinophils.

The applicant therefore sought to find a reagent which effectively lyses all blood cells except the basophil granulocytes or the eosinophil granulocytes, and which offers characteristics which are compatible with the automation of cytology counting methods.

SUMMARY OF THE INVENTION

The applicant found that an ether of polyoxyethylene and of a fatty alcohol can produce specific, effective lysis of blood cells other than the eosinophil and basophil granulocytes which is sufficiently rapid to be automated.

The applicant also found, in surprising manner, that depending upon the pH of the medium in which the blood sample is treated, it is possible to differentiate either the basophil granulocytes or the eosinophil granulocytes.

The object of the present invention is therefore a method for differentiating and isolating sub-populations of leucocytes in a blood sample, characterized in that said sample is treated with polyoxyethylene 9-lauryl ether.

This method allows various sub-populations of leucocytes to be distinguished by modulating the lysis reaction.

Also, if lysis of the majority of erythrocytes and leucocyte sub-groups is obtained, it is possible, according to the pH of the reaction medium, to differentiate either the sub-group of basophil granulocyes or the sub-group of eosinophil granulocytes.

Therefore, if the method is carried out at an acid pH, that is to say at a pH advantageously lying between 2 and 3.5, preferably between 2.5 and 3.1, the basophil granulocytes are isolated in majority in the blood sample. For the present invention it is considered that a sample comprises in majority a given cell type, when this cell type constitutes at least 99% of the intact cells in the sample.

If the method is carried out at a basic pH, that is to say advantageously between 9 and 10, preferably between 9.50 and 9.70, the cells isolated in majority in the blood sample are eosinophil granulocytes.

The present invention also relates to a reagent for implementing the method described above, characterized in that it comprises from 0.1 to 10 g/l, preferably from 0.5 to 5 g/l of polyoxyethylene 9-lauryl ether.

Such reagent can thus be used for differentiating and isolating granulocyte cells, eosinophils and basophils.

It advantageously comprises, for the isolation of basophil granulocytes, phthalic acid and/or hydrochloric acid. It therefore advantageously comprises from 0.5 to 3 g/l of phthalic acid, preferably from 1 to 2 g/l. Hydrochloric acid can be added, in relation to the quantities of phthalic acid, in order to have an acid pH, preferably between 2 and 3.5.

For the isolation of eosinophil granulocytes, the lysis solution may comprise, in addition to polyoxyethylene 9-lauryl ether, sodium hydroxide and sodium tetraborate.

Finally, the present invention relates to a method for counting sub-populations of leucocytes in a blood sample, characterized in that said sample is treated according to the method described above, and the cells which have not been lysed are counted.

DETAILS

The method of differentiation and isolation according to the present invention may be implemented by simply mixing, preferably between 20° C. and 60° C., especially at 40° C., a blood sample and a reagent whose composition was given above;

Advantageously, the sample:reagent ratio lies between 1:125 and 1:150.

The cells which are not lysed can be counted by any means available to the man skilled in the art, in particular by measuring impedance.

Polyoxyethylene 9-lauryl ether can be obtained from the Sigma company (La Verpillière, France) which markets the product under reference P 9641.

The present method may in particular be implemented on cytometric counting apparatus marketed by the Sysmex and ABX companies, or by the applicant, and in general on counters which use the principle of measuring resistivity (impedance).

The present method offers the following advantages:

it provides selective, rapid lysis of all red cells present in the sample and of white cell populations with the exception of basophil granulocytes, in an acid medium, and of eosinophil granulocytes in a basic medium.

the lysates of the blood samples treated according to this method have negligible quantities of debris in comparison with the methods described in the prior art, and it is reproducible, it achieves lysis of the cells, other than the eosinophils or basophils, within a sufficiently short period of time to allow the method to be adapted for use on automated cytometric counters or automated haematology apparatus, it only requires one lysis product, polyoxyethylene 9-lauryl ether, which considerably simplifies the formulation of reagents.

The present invention is illustrated by the following example:

EXAMPLE

Isolation and Differentiation of Basophil Granulocytes

The blood sample, in a volume of 30 μl, is treated with 4 ml of reagent having the following composition:

| Polyoxyethylene 9-lauryl ether: | 2 g/l |
|---|---|
| Phthalic acid | 1.5 g/l |
| 1N HCl: | Sufficient to obtain a pH of 2.8 |
| Distilled water: | Sufficient to make up to 1 liter |

An anti-oxidant and a preservative agent may be added to this reagent.

The reaction was carried out at a temperature of 40° C.

Immediate lysis of the erythrocytes was observed, followed by progressive lysis of all the leucocytes with the exception of the basophil granulocytes. The lysis time was 15 seconds.

The sample thus treated was analyzed on a HYCEL HEMA 5 automated cytometer.

Analysis showed that the method according to the invention can allow differentiation between the basophil granulocytes and cell debris.

A second sample was treated under the same conditions for 30 seconds. Microscopic examination verified that only the basophil granulocytes remained intact, which confirmed the selectivity of this lysis reagent.

I claim:

1. In a method for differentiating and isolating a subpopulation of leucocytes in a blood sample by treating the sample with a reagent comprising a surface active agent, the improvement wherein the surface active agent consists essentially of polyoxyethylene 9-lauryl ether.

2. A method according to claim 1 wherein basophil granulocytes are differentiated and isolated by treating said sample in an acid medium.

3. A method according to claim 2 wherein the acid medium has a pH between 2 and 3.5.

4. A method according to claim 3 wherein the acid medium has a pH between 2.5 and 3.1.

5. A method according to claim 1 wherein eosinophil granulocytes are differentiated and isolated by treatment in a basic medium.

6. A method according to claim 5 wherein the basic medium has a pH between 9 and 10.

7. A method according to claim 5 wherein the basic medium has a pH between 9.50 and 9.70.

8. A method according to claim 1 wherein the reagent is a reagent for specific lysis of erythrocytes and which preserves the integrity of leucocyte subpopulations, said reagent comprising from 0.1 to 10 g/l of polyoxyethylene 9-lauryl ether.

9. A method according to claim 1 wherein the reagent is a reagent for specific lysis of erythrocytes and which preserves the integrity of leucocyte subpopulations, said reagent comprising from 0.5 to 5 g/l of polyoxyethylene 9-lauryl ether.

10. A method according to claim 1 wherein the reagent comprises from 0.5 to 5 g/l of polyoxyethylene 9-lauryl ether and further comprises a member selected from the group consisting of phthalic acid and hydrochloric acid.

11. A method according to claim 10 wherein the reagent comprises from 0.5 to 3 g/l of phthalic acid.

12. A method according to claim 11 wherein the reagent comprises from 1 to 2 g/l of phthalic acid.

13. A method for counting leucocyte subpopulations in a blood sample which comprises a) a method of claim 11 and b) counting non-lysed cells.

14. A reagent for specific lysis of erythrocytes and which preserves the integrity of leucocyte subpopulations, the reagent comprising from 0.1 to 10 g/l of surface active agent which consists essentially of polyoxyethylene 9-lauryl ether and from 0.5 to 3 g/l of phthalic acid.

15. A reagent according to claim 14 which comprises from 1 to 2 g/l of phthalic acid.

* * * * *